US008486033B2

(12) United States Patent
Orgill et al.

(10) Patent No.: US 8,486,033 B2
(45) Date of Patent: Jul. 16, 2013

(54) APPLICATION OF POLYMERIC MATERIALS TO SCREENS TO FACILITATE HEMOSTASIS AND WOUND HEALING

(75) Inventors: Dennis P. Orgill, Belmont, MA (US); Giorgio Pietramaggiori, Modena (IT); Sergio Finkielsztein, Newton, MA (US); John N. Vournakis, Charleston, SC (US)

(73) Assignees: Marine Polymer Technologies, Inc., Danvers, MA (US); Brigham & Women's Hospital, Inc., Boston, MA (US)

( * ) Notice: Subject to any disclaimer, the term of this patent is extended or adjusted under 35 U.S.C. 154(b) by 510 days.

(21) Appl. No.: 12/761,837

(22) Filed: Apr. 16, 2010

(65) Prior Publication Data

US 2011/0015586 A1 Jan. 20, 2011

Related U.S. Application Data

(63) Continuation-in-part of application No. 12/175,777, filed on Jul. 18, 2008, now abandoned.

(60) Provisional application No. 60/959,932, filed on Jul. 18, 2007.

(51) Int. Cl.
*A61M 1/00* (2006.01)

(52) U.S. Cl.
USPC .............................. 604/313; 514/62

(58) Field of Classification Search
USPC ............ 604/304, 305, 313, 367–370; 602/46, 602/48, 50, 53, 56; 424/93.7, 93.72, 443, 424/445, 488; 514/54
See application file for complete search history.

(56) References Cited

U.S. PATENT DOCUMENTS

| | | | |
|---|---|---|---|
| 3,914,413 A | 10/1975 | Balassa | |
| 5,623,064 A | 4/1997 | Vournakis et al. | |
| 5,636,643 A | 6/1997 | Argenta et al. | |
| 5,645,081 A | 7/1997 | Argenta et al. | |
| 6,864,245 B2 | 3/2005 | Vournakis et al. | |
| 2002/0019367 A1* | 2/2002 | Vournakis et al. | 514/54 |
| 2003/0208149 A1 | 11/2003 | Coffey | |
| 2004/0001878 A1 | 1/2004 | DeBusk et al. | |
| 2004/0120993 A1 | 6/2004 | Zhang et al. | |
| 2004/0220140 A1* | 11/2004 | Vournakis et al. | 514/54 |
| 2007/0027414 A1 | 2/2007 | Hoffman et al. | |
| 2007/0032754 A1 | 2/2007 | Walsh | |
| 2007/0032755 A1 | 2/2007 | Walsh | |
| 2007/0225663 A1 | 9/2007 | Watt et al. | |
| 2009/0117175 A1* | 5/2009 | Finkielsztein et al. | 424/445 |
| 2009/0149823 A1 | 6/2009 | Orgill et al. | |

FOREIGN PATENT DOCUMENTS

| | | |
|---|---|---|
| EP | 0918548 | 6/1999 |
| WO | 9420041 | 9/1994 |
| WO | 2005123170 | 12/2005 |
| WO | 2007016664 | 2/2007 |

OTHER PUBLICATIONS

International Search Report dated Dec. 27, 2011 relating to International Application No. PCT/US2011/032434.
Argenta et al., Vacuum-assisted closure: a new method for wound control and treatment: clinical experience. Ann Plast Surg. Jun. 1997;38(6):563-76.
Armstrong et al., Diabetic Foot Study Consortium. Negative pressure wound therapy after partial diabetic foot amputation: a multicentre, randomised controlled trial. Lancet. Nov. 12, 2005;366(9498):1704-10.
Cavanagh et al.,Treatment for diabetic foot ulcers. Lancet. Nov. 12, 2005;366(9498):1725-35.
Edington et al., A prospective randomized evaluation of negative pressure wound dressing for diabetic foot wounds. Ann Vasc Surg. 2003;17;546.
"Falanga, Wound healing and its impairment in the diabetic foot. Lancet. Nov. 12, 2005;366(9498):1736-43."
Fazio et al., Reduction in adhesive small-bowel obstruction by Seprafilm adhesion barrier after intestinal resection. Dis Colon Rectum. Jan. 2006;49(1):1-11.
"Fischer et al., Synergistic platelet integrin signaling and factor XII activation in poly-N-13 acetyl glucosamine fiber-mediated hemostasis. Biomaterials. Sep. 2005;26(27):5433-43."
Fischer et al., Comparison of structural and hemostatic properties of the poly-N-acetyl glucosamine Syvek Patch with products containing chitosan. Microsc Res Tech. Feb. 15, 2004;63(3):168-74.
Fischer et al., Non-classical processes in surface hemostasis: mechanisms for the poly-N-acetyl glucosamine-induced alteration of red blood cell morphology and surface prothrombogenicity. Biomed Mater. Mar. 2008;3(1):015009. Epub Feb. 6, 2008.
Gerstein et al., Why don't pigs get diabetes? Explanations for variations in diabetes susceptibility in human populations living in a diabetogenic environment. CMAJ. Jan. 3, 2006;174(1):25-6.
International Preliminary Report on Patentability mailed Oct. 26, 2012 for Application No. PCT/US2011/032434 (6 Pages).
Jemal et al., Trends in the leading causes of death in the United States, 1970-2002. JAMA. Sep. 14, 2005;294 (10):1255-9.
Joseph et al., A prospective randomized trail of vacuum-assisted closure versus standard therapy of chronic nonhealing wounds. Wounds. 2000;12:60. Abstract only.
Lane, Epidemiology, etiology, and diagnosis of osteoporosis. Am J Obstet Gynecol. Feb. 2006;194(2 Suppl):S3-11.
Malette et al., Johnson ND, Rainer WG. Chitosan: a new hemostatic. Ann Thorac Surg. Jul. 1983;36(1):55-8.
Morykwas et al., Vacuum-assisted closure: a new method for wound control and treatment: animal studies and basic foundation. Ann Plast Surg. Jun. 1997;38(6):553-62.
Najjar et al., Evaluation of poly-N-acetyl glucosamine as a hemostatic agent in patients undergoing cardiac catheterization: a double-blind, randomized study. J Trauma. Jul. 2004;57(1 Suppl):S38-41.

(Continued)

*Primary Examiner* — Melanie Hand
(74) *Attorney, Agent, or Firm* — Nutter McClennen & Fish LLP

(57) ABSTRACT

This invention relates in general to a method and device for facilitating hemostasis and wound healing. In particular, the invention relates to the device comprising a polymeric material disposed on a scaffold that facilitates hemostasis and wound healing. Specifically, the invention contemplates the use of such scaffolds in conjunction with a negative pressure device.

27 Claims, 11 Drawing Sheets

OTHER PUBLICATIONS

Orgill et al., Global surgery—future directions. Microdeformational wound therapy—a new era in wound healing. Business Briefing. 2005:22-25.

Orgill et al., The use of collagen-GAG membranes in reconstructive surgery. Ann N Y Acad Sci. Oct. 30, 1999;888:233-48.

Peña Ede et al., Elastoviscous substances with analgesic effects on joint pain reduce stretch-activated ion channel activity in vitro. Pain. Oct. 2002;99(3):501-8.

Pietramaggiori et al., Effects of poly-N-acetyl glucosamine (pGlcNAc) patch on wound healing in db/db mouse. J Trauma. Mar. 2008;64(3):803-8.

Saxena et al., Vacuum-assisted closure: microdeformations of wounds and cell proliferation. Plast Reconstr Surg. Oct. 2004;114(5):1086-96.

Smith et al., Differential effect of materials for surface hemostasis on red blood cell morphology. Microsc Res Tech. Oct. 2008;71(10): 721-9.

Thatte et al., Mechanisms of poly-N-acetyl glucosamine polymer-mediated hemostasis: platelet interactions. J Trauma. Jul. 2004;57(1 Suppl):S13-21.

Thatte et al., Poly-N-acetyl glucosamine-mediated red blood cell interactions. J Trauma. Jul. 2004;57(1 Suppl):S7-12.

Ulbrecht et al., Foot problems in diabetes: an overview. Clin Infect Dis. Aug. 1, 2004;39 Suppl 2:S73-82.

Vournakis et al., Isolation, purification, and characterization of poly-N-acetyl glucosamine use as a hemostatic agent. J Trauma. Jul. 2004;57(1 Suppl):S2-6.

Vournakis et al., Poly-N-acetyl glucosamine nanofibers regulate endothelial cell movement and angiogenesis: dependency on integrin activation of Ets1. J Vasc Res. 2008;45(3):222-32. Epub Dec. 19. 2007.

U.S. Office Action for U.S. Appl. No. 12/175,777, issued Aug. 1, 2012 (16 pages).

U.S. Office Action for U.S. Appl. No. 12/175,777, issued Mar. 10, 2011 (13 pages).

* cited by examiner

TABLE I
Animal Weights and Clinical Observations

Test Article:   MP719

Lot/Batch No.:  Not Supplied by Sponsor

4 Week Implantation

| Animal No. | Sex | Body Weight (kg) | | Weight Change | Signs of Toxicity* |
|---|---|---|---|---|---|
| | | Day 0 08/29/2006 | Day 28 09/26/2006 | | |
| 60959 | Male | 2.93 | 3.47 | 0.54 | None |
| 60961 | Male | 3.05 | 3.36 | 0.31 | None |
| 60968 | Female | 3.18 | 3.60 | 0.42 | None |

* Summary of Clinical Observations from Day 0 through Day 28.

FIG. 2

TABLE II
Macroscopic Observations
4 Week Implantation

Test Article: MP719

Lot/Batch No.: Not Supplied by Sponsor

Animal No.: 60959

| Tissue Site: | T1 | T2 | T3 | T4 | Test Ave. | C1-1 | C1-2 | C1-3 | C1-4 | Control C1 Ave. | C2-1 | C2-2 | C2-3 | C2-4 | Control C2 Ave. |
|---|---|---|---|---|---|---|---|---|---|---|---|---|---|---|---|
| Inflammation | 0 | NSF | 0 | NSF | 0 | NSF | NSF | NSF | NSF | N/A | 0 | 0 | 0 | 0 | 0 |
| Encapsulation | 0 | NSF | 0 | NSF | 0 | NSF | NSF | NSF | NSF | N/A | 0 | 0 | 0 | 0 | 0 |
| Hemorrhage | 0 | NSF | 0 | NSF | 0 | NSF | NSF | NSF | NSF | N/A | 0 | 0 | 0 | 0 | 0 |
| Necrosis | 0 | NSF | 0 | NSF | 0 | NSF | NSF | NSF | NSF | N/A | 0 | 0 | 0 | 0 | 0 |
| Discoloration | 0 | NSF | 0 | NSF | 0 | NSF | NSF | NSF | NSF | N/A | 0 | 0 | 0 | 0 | 0 |
| Total | 0 | N/A | 0 | N/A |  | N/A | N/A | N/A | N/A |  | 0 | 0 | 0 | 0 |  |

Animal No.: 60961

| Tissue Site: | T1 | T2 | T3 | T4 | Test Ave. | C1-1 | C1-2 | C1-3 | C1-4 | Control C1 Ave. | C2-1 | C2-2 | C2-3 | C2-4 | Control C2 Ave. |
|---|---|---|---|---|---|---|---|---|---|---|---|---|---|---|---|
| Inflammation | NSF | NSF | NSF | NSF | N/A | NSF | NSF | NSF | NSF | N/A | 0 | 0 | NSF | 0 | 0 |
| Encapsulation | NSF | NSF | NSF | NSF | N/A | NSF | NSF | NSF | NSF | N/A | 0 | 0 | NSF | 0 | 0 |
| Hemorrhage | NSF | NSF | NSF | NSF | N/A | NSF | NSF | NSF | NSF | N/A | 0 | 0 | NSF | 0 | 0 |
| Necrosis | NSF | NSF | NSF | NSF | N/A | NSF | NSF | NSF | NSF | N/A | 0 | 0 | NSF | 0 | 0 |
| Discoloration | NSF | NSF | NSF | NSF | N/A | NSF | NSF | NSF | NSF | N/A | 0 | 0 | NSF | 0 | 0 |
| Total | N/A | N/A | N/A | N/A |  | N/A | N/A | N/A | N/A |  | 0 | 0 | N/A | 0 |  |

Animal No.: 60968

| Tissue Site: | T1 | T2 | T3 | T4 | Test Ave. | C1-1 | C1-2 | C1-3 | C1-4 | Control C1 Ave. | C2-1 | C2-2 | C2-3 | C2-4 | Control C2 Ave. |
|---|---|---|---|---|---|---|---|---|---|---|---|---|---|---|---|
| Inflammation | NSF | NSF | NSF | NSF | N/A | NSF | NSF | NSF | NSF | N/A | 0 | 0 | 0 | 0 | 0 |
| Encapsulation | NSF | NSF | NSF | NSF | N/A | NSF | NSF | NSF | NSF | N/A | 0 | 0 | 0 | 0 | 0 |
| Hemorrhage | NSF | NSF | NSF | NSF | N/A | NSF | NSF | NSF | NSF | N/A | 0 | 0 | 0 | 0 | 0 |
| Necrosis | NSF | NSF | NSF | NSF | N/A | NSF | NSF | NSF | NSF | N/A | 0 | 0 | 0 | 0 | 0 |
| Discoloration | NSF | NSF | NSF | NSF | N/A | NSF | NSF | NSF | NSF | N/A | 0 | 0 | 0 | 0 | 0 |
| Total | N/A | N/A | N/A | N/A |  | N/A | N/A | N/A | N/A |  | 0 | 0 | 0 | 0 |  |

T = test site (representative sections were submitted for microscopic assessment)
C1 = Surgicel (Due to the nature of the material, representative sections were submitted for microscopic assessment)
C2 = Negative Control High Density Polyethylene (Negative Control Plastic)

Grading Scale

0 = no reaction  2 = moderate reaction  NSF = No Site Found
1 = mild reaction  3 = marked reaction  N/A = Not Applicable

FIG. 3

TABLE III
Microscopic Observations
4 Week Implantation

Test Article:  MP719

Lot/Batch No.: Not Supplied by Sponsor

Animal No.:  60959

| Categories | Test Sites** | | | Control Sites | | | | | | | |
|---|---|---|---|---|---|---|---|---|---|---|---|
| Reaction | T1 | T2 | T3 | C1-1 | C1-2 | C1-3 | C1-4 | C2-1 | C2-2 | C2-3 | C2-4 |
| Foreign Debris | 0.0 | 0.0 | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 | 0.5 | 0.5 |
| * Polymorphs | 0.0 | 0.5 | 0.5 | 0.0 | 0.0 | 0.0 | 0.0 | 0.0 | 0.0 | 0.0 | 0.0 |
| * Lymphocytes | 0.0 | 0.0 | 0.0 | 0.0 | 0.0 | 0.0 | 0.0 | 0.0 | 0.0 | 0.0 | 0.0 |
| * Eosinophils | 0.0 | 0.0 | 0.0 | 0.0 | 0.0 | 0.0 | 0.0 | 0.0 | 0.0 | 0.0 | 0.0 |
| * Plasma Cells | 0.0 | 0.0 | 0.0 | 0.0 | 0.0 | 0.0 | 0.0 | 0.0 | 0.0 | 0.0 | 0.0 |
| * Macrophages | 0.5 | 0.5 | 0.5 | 0.5 | 0.5 | 0.5 | 0.5 | 0.5 | 0.5 | 0.5 | 0.5 |
| * Giant Cells | 0.0 | 0.0 | 0.0 | 0.0 | 0.0 | 0.0 | 0.0 | 0.0 | 0.0 | 0.0 | 0.0 |
| * Degeneration | 0.5 | 0.5 | 0.5 | 0.5 | 0.0 | 0.5 | 0.0 | 0.0 | 0.0 | 0.0 | 0.0 |
| * Necrosis | 0.0 | 0.0 | 0.0 | 0.0 | 0.0 | 0.0 | 0.0 | 0.0 | 0.0 | 0.0 | 0.0 |
| * Fibrosis | 0.5 | 0.5 | 0.5 | 0.5 | 0.5 | 0.5 | 0.5 | 0.5 | 0.5 | 0.5 | 0.5 |
| * Fatty Infiltrate | 0.0 | 0.0 | 0.5 | 0.0 | 0.5 | 0.0 | 0.5 | 0.5 | 0.5 | 0.0 | 0.5 |
| Total | 1.5 | 2.0 | 2.5 | 1.5 | 1.5 | 1.5 | 1.5 | 1.5 | 1.5 | 1.0 | 1.5 |

T = Test Site
C1 = Surgicel
C2 = Negative Control High Density Polyethylene (Negative Control Plastic)

Animal Test Score (Average*) =   2.0
Animal C1 Score (Average*) =   1.5
Animal C2 Score (Average*) =   1.4

Animal Score (Average Test Score - Average C1 Score) =   0.5
Animal Score (Average Test Score - Average C2 Score) =   0.6

* Used in calculation of Bioreactivity Rating.
** No site found in T4.

FIG. 4A

TABLE III
Microscopic Observations (Cont.)
4 Week Implantation

Test Article: MP719

Lot/Batch No.: Not Supplied by Sponsor

Animal No.: 60961

| Categories | Test Sites** | | | Control Sites** | | | | | |
|---|---|---|---|---|---|---|---|---|---|
| Reaction | T1 | T3 | T4 | C1-1 | C1-3 | C1-4 | C2-1 | C2-2 | C2-3 |
| Foreign Debris | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 |
| * Polymorphs | 0.0 | 0.0 | 0.5 | 0.5 | 0.0 | 0.5 | 0.5 | 0.5 | 0.5 |
| * Lymphocytes | 0.0 | 0.0 | 0.0 | 0.0 | 0.0 | 0.0 | 0.0 | 0.0 | 0.0 |
| * Eosinophils | 0.0 | 0.0 | 0.0 | 0.0 | 0.0 | 0.0 | 0.0 | 0.0 | 0.0 |
| * Plasma Cells | 0.0 | 0.0 | 0.0 | 0.0 | 0.0 | 0.0 | 0.0 | 0.0 | 0.0 |
| * Macrophages | 0.5 | 0.5 | 0.5 | 0.5 | 0.5 | 0.5 | 0.5 | 0.5 | 0.5 |
| * Giant Cells | 0.0 | 0.0 | 0.0 | 0.0 | 0.0 | 0.0 | 0.0 | 0.0 | 0.0 |
| * Degeneration | 0.5 | 0.5 | 0.5 | 0.5 | 0.5 | 0.5 | 0.5 | 0.5 | 0.5 |
| * Necrosis | 0.0 | 0.0 | 0.0 | 0.0 | 0.0 | 0.0 | 0.0 | 0.0 | 0.0 |
| * Fibrosis | 0.5 | 0.5 | 0.5 | 0.5 | 0.5 | 0.5 | 0.5 | 0.5 | 0.5 |
| * Fatty Infiltrate | 0.0 | 0.5 | 0.0 | 0.5 | 0.0 | 0.5 | 0.5 | 0.5 | 0.5 |
| Total | 1.5 | 2.0 | 2.0 | 2.5 | 1.5 | 2.5 | 2.5 | 2.5 | 2.5 |

T = Test Site
C1 = Surgical
C2 = Negative Control High Density Polyethylene (Negative Control Plastic)

Animal Test Score (Average*) = 1.8
Animal C1 Score (Average*) = 2.2
Animal C2 Score (Average*) = 2.5

Animal Score (Average Test Score - Average C1 Score) = -0.4
Animal Score (Average Test Score - Average C2 Score) = -0.7

* Used in calculation of Bioreactivity Rating.
** No site found in T2, C1-2, and C2-4.

FIG. 4B

TABLE III
Microscopic Observations (Cont.)
4 Week Implantation

Test Article: MP719

Lot/Batch No. Not Supplied by Sponosr

Animal No.: 60968

| Categories | Test Sites | | | | Control Sites** | | | | | | |
|---|---|---|---|---|---|---|---|---|---|---|---|
| Reaction | T1 | T2 | T3 | T4 | C1-1 | C1-2 | C1-3 | C2-1 | C2-2 | C2-3 | C2-4 |
| Foreign Debris | 0.0 | 0.0 | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 | 0.5 | 0.5 |
| * Polymorphs | 0.0 | 0.5 | 0.0 | 0.5 | 0.0 | 0.0 | 0.0 | 0.5 | 0.5 | 0.0 | 0.5 |
| * Lymphocytes | 0.0 | 0.0 | 0.0 | 0.0 | 0.0 | 0.0 | 0.0 | 0.0 | 0.0 | 0.0 | 0.0 |
| * Eosinophils | 0.0 | 0.0 | 0.0 | 0.0 | 0.0 | 0.0 | 0.0 | 0.0 | 0.0 | 0.0 | 0.0 |
| * Plasma Cells | 0.0 | 0.0 | 0.0 | 0.0 | 0.0 | 0.0 | 0.0 | 0.0 | 0.0 | 0.0 | 0.0 |
| * Macrophages | 0.5 | 0.5 | 0.5 | 0.5 | 0.5 | 0.5 | 0.5 | 0.5 | 0.5 | 0.5 | 0.5 |
| * Giant Cells | 0.0 | 0.0 | 0.0 | 0.0 | 0.0 | 0.0 | 0.0 | 0.0 | 0.0 | 0.0 | 0.0 |
| * Degeneration | 0.5 | 0.5 | 0.5 | 0.5 | 0.5 | 0.5 | 0.5 | 0.5 | 0.5 | 0.5 | 0.5 |
| * Necrosis | 0.0 | 0.0 | 0.0 | 0.0 | 0.0 | 0.0 | 0.0 | 0.0 | 0.0 | 0.0 | 0.0 |
| * Fibrosis | 0.5 | 0.5 | 0.5 | 0.5 | 0.5 | 0.5 | 0.5 | 0.5 | 0.5 | 0.5 | 0.5 |
| * Fatty Infiltrate | 0.5 | 0.5 | 0.5 | 0.5 | 0.5 | 0.0 | 0.5 | 0.5 | 0.5 | 0.5 | 0.5 |
| Total | 2.0 | 2.5 | 2.0 | 2.5 | 2.0 | 1.5 | 2.0 | 2.5 | 2.5 | 2.0 | 2.5 |

T = Test Site
C1 = Surgicel
C2 = Negative Control High Density Polyethylene (Negative Control Plastic)

Animal Test Score (Average*) = 2.3
Animal C1 Score (Average*) = 1.8
Animal C2 Score (Average*) = 2.4

Animal Score (Average Test Score - Average C1 Score) = 0.5
Animal Score (Average Test Score - Average C2 Score) = -0.1

* Used in calculation of Bioreactivity Rating.
** No site found in C1-4.

|  | C1 | C2 |
|---|---|---|
| Animal Score 60759 = | 0.5 | 0.6 |
| Animal Score 60961 = | -0.4 | -0.7 |
| Animal Score 60968 = | 0.5 | -0.1 |

Bioreactivity Rating = 0.2 = No Reaction
Bioreactivity Rating = -0.1 = No Reaction

FIG. 4C

FIG. 6
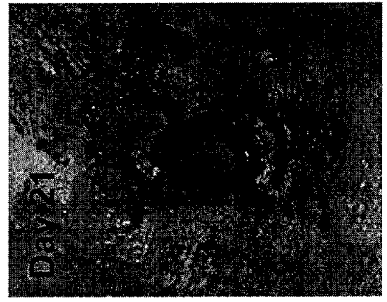
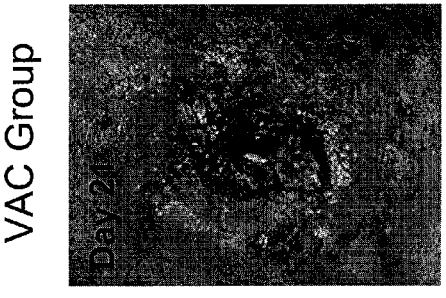
VAC Group
Tn-24 Group
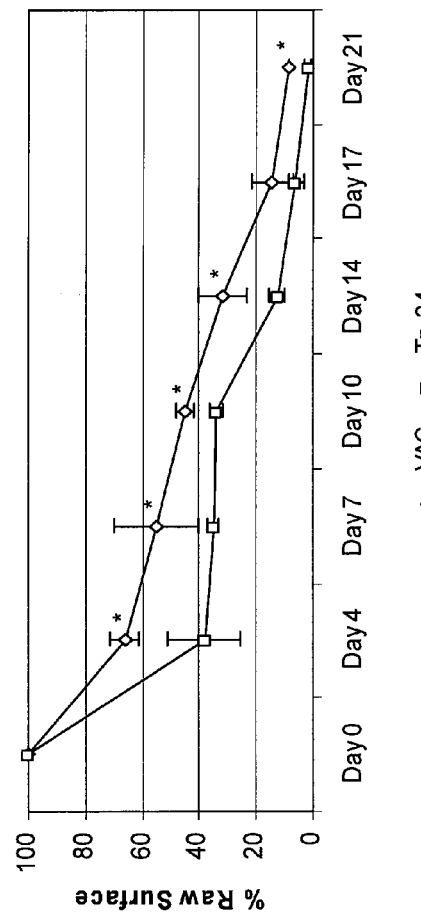
Wound Epithelialization
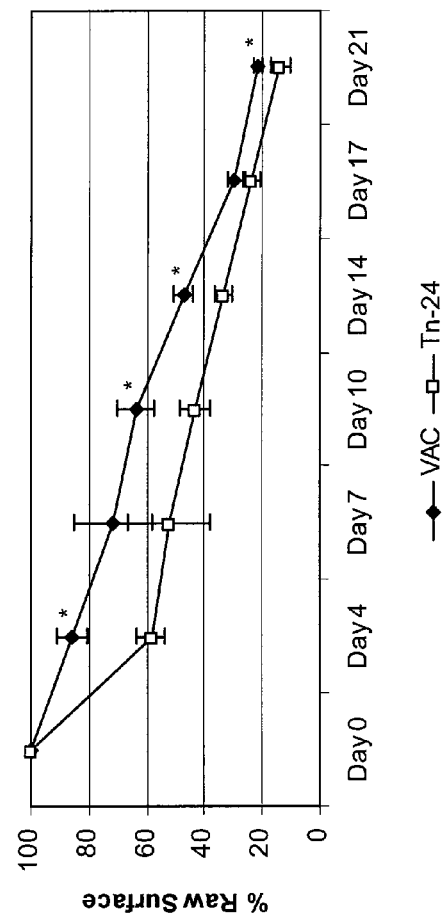
Wound Contraction

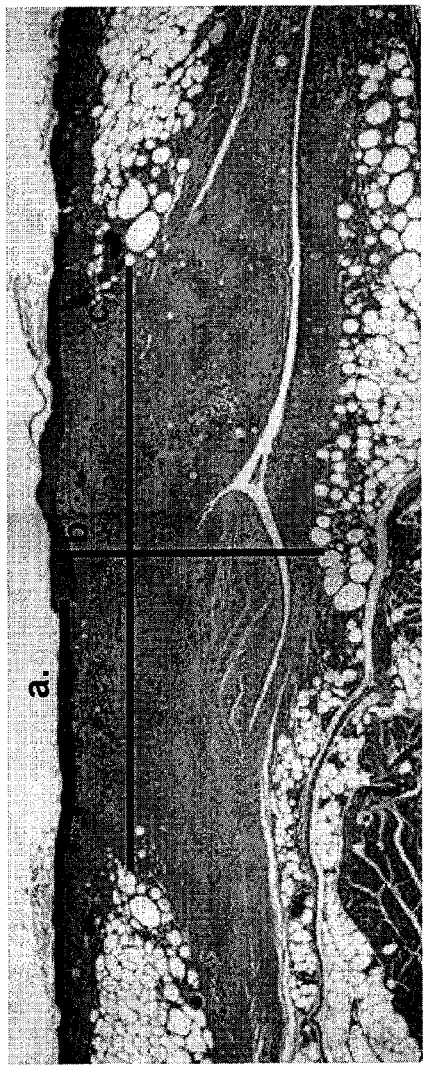
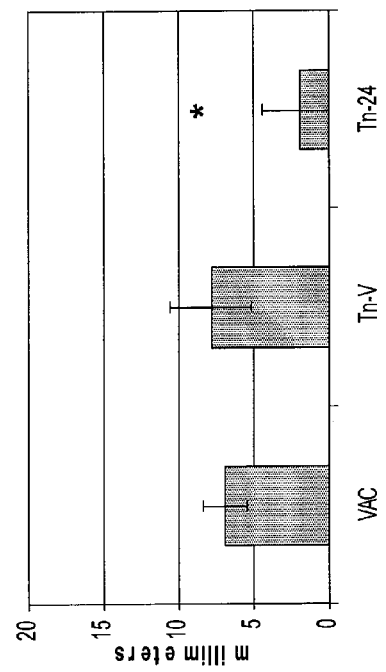
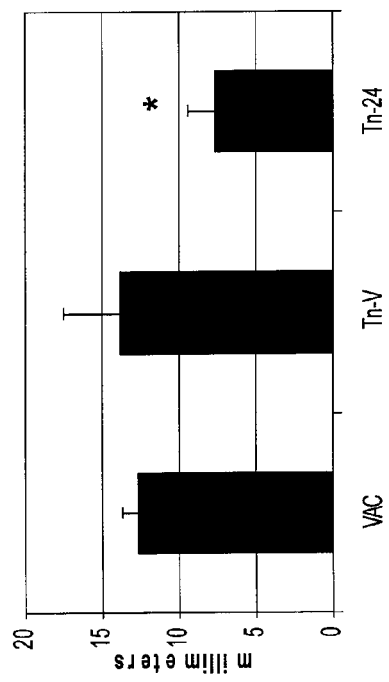
FIG. 7

APPLICATION OF POLYMERIC MATERIALS TO SCREENS TO FACILITATE HEMOSTASIS AND WOUND HEALING

PRIORITY OF THE INVENTION

The present invention claims priority to U.S. Pat. application Ser. No. 12/175,777 filed Jul. 18, 2008 which in turn claims priority to U.S. Provisional Application No. 60/959,932 filed Jul. 18, 2007 all entitled "APPLICATION OF POLYMERIC MATERIALS TO SCREENS TO FACILITATE HEMOSTASIS AND WOUND HEALING.", which are hereby incorporated by reference.

FIELD OF THE INVENTION

This invention relates in general to a method and device for facilitating hemostasis and wound healing. In particular, the invention relates to the device comprising a polymeric material disposed on a scaffold that facilitates hemostasis and wound healing. Specifically, the invention contemplates the use of such scaffolds in conjunction with a negative pressure device.

BACKGROUND OF THE INVENTION

While improvements in diagnostic tools and therapies have led to decreased morbidity from heart disease, cancer and stroke (Jemal, A., Ward, E., Hao, Y. & Thun, M. Trends in the leading causes of death in the United States, 1970-2002. *Jama* 294, 1255-9, 2005), the epidemic of diabetes (Gerstein, H. C. & Waltman, L. Why don't pigs get diabetes? Explanations for variations in diabetes susceptibility in human populations living in a diabetogenic environment. *Cmaj* 174, 25-6 2006) and the aging population (Lane, N. E. Epidemiology, etiology, and diagnosis of osteoporosis. *Am J Obstet Gynecol* 194, S3-11 2006) are now posing a critical challenge for wound care. (Cavanagh, P. R., Lipsky, B. A., Bradbury, A. W. & Botek, G. Treatment for diabetic foot ulcers. *Lancet* 366, 1725-35 2005); (Falanga, V. Wound healing and its impairment in the diabetic foot. *Lancet* 366, 1736-43 2005). Frequent in this population is the use of anticoagulants. Also many wounds in their inflammatory state can have significant bleeding even in the presence of normal clotting parameters. Equipment and techniques for accelerating wound healing have critical in the care of these patients. The availability of device or system that would enhance both clotting and wound healing might would be a significant advance in treatment.

Suction has a long been a valuable tool in wound healing. The use of suction and related techniques in wound treatment has been well characterized in the literature. (See., e.g., Charikar and Jeter, Orringer, Wooding-Scott). Chest tubes, for example, re-approximate the parietal and visceral pleura while suction drains facilitate closure of large surgical spaces.

A recent improvement over suction alone in treating wounds has been the introduction of negative pressure or sub-atmospheric therapy systems as exemplified by the Vacuum Assisted Closure (VAC) systems of Argenta and Morykwas. (Argenta, L. C., Morykwas, M. J. Vacuum-assisted closure: a new method of wound control and treatment: clinical experience. *Ann. Plast. Surg.* 38: 563, 1997); (Morykwas, M. J., Argenta, L. C., Shelton-Brown, E. I., et al. Vacuum-assisted closure: a new method for wound control and treatment: animal studies and basic foundation. *Ann. Plast. Surg.* 38: 553, 1997); U.S. Pat. No. 5,636,643; U.S. Pat. No. 5,645,081). Argenta et al. found that the controlled distribution of pressure throughout the wound is important in speeding wound healing. In the original design the negative pressure was distributed over a mesh applied directly to the wound site.

The VAC system has become the preferred method in many centers for treating a wide array of complex wounds. In its current commercial embodiment the VAC is a system comprising a vacuum pump that delivers sub-atmospheric pressure to a polyurethane ether open pore foam (400-600 µm) covered by an occlusive polyurethane drape. It includes an open pore polyurethane foam in contact with the wound site, a semi-occlusive drape, and a suction tube in addition to the vacuum or suction pump. Several prospective studies have shown that the VAC system increases the healing of chronic wounds at least twice as rapidly as conventional methods such as wet to dry dressing changes. (Joseph, E., Hamori, C. A., Bergman, S., et al. A prospective randomized trail of vacuum-assisted closure versus standard therapy of chronic nonhealing wounds. *Wounds* 12: 60, 2000); (Edington, M. T., Brown, K. R., Seabrook, B. R., et al. A prospective randomized evaluation of negative pressure wound dressing for diabetic foot wounds. *Ann. Vasc. Surg.* 17: 645, 2003). Clinicians noted a rapid change in the wounds including overall shrinkage and induction of granulation tissue (Edington, M. T., Brown, K. R., Seabrook, B. R., et al. A prospective randomized evaluation of negative pressure wound dressing for diabetic foot wounds. *Ann. Vasc. Surg.* 17: 645, 2003); (Saxena, V., Hwang, C. W., Huang, S., et al. Vacuum-assisted closure: microdeformations of wounds and cell proliferation. *Plast. Reconstr. Surg.* 114: 1086, 2004).

Despite the commercial success of the device, it has certain limitations. One major limitation is that unless bleeding is completely stopped prior to use of the device, bleeding at the wound will continue or increase, often requiring removal of the VAC device. This has become particularly problematic given the increasing number of patients are on anticoagulants such as Coumadin, Heparin, Lovenox, Plavix and Aspirin. Having an effective method of obtaining hemostasis would be a great advantage to the VAC device in selected patients. Therefore a negative pressure wound device that incorporates hemostatic characteristics would be of great value to the wound care community.

There are many hemostatic agents currently on the market including micro-fibrillar collagen, oxidized regenerated cellulose, and lyophilized gelatin. Each of these agents can help with hemostasis, but in general, clinicians are reluctant to use these in many wounds because of the foreign body response that they can cause. Other methods such as fibrin glue are expensive and have at least a theoretical risk of viral transmission.

In addition, it would be preferable if the hemostatic agent used in such an application itself had a wound healing enhancing effect. Some hemostatic agents may provide control of hemorrhage and have a low foreign body response (as shown by favorable performance in an ISO implantation test) however it may have a negative wound healing effect. (E.g., Surgicel device manufactured by Ethicon, Inc.)

Therefore an appliance incorporating a hemostatic agent that could be incorporated into a negative pressure wound care device such as the VAC, that would also enhance (or at least not change) the efficacy of the device and would not induce significant foreign body response is highly desirable.

Highly homogeneous and pure poly-N-acetyl glucosamine (pGlcNAc) nanofibers can be isolated by the culture of a marine microalga. (Vournakis J N, Demcheva M, Whitson A, Guirca R, Pariser E R. Isolation, purification, and characterization of poly-N-acetyl glucosamine use as a hemostatic agent. *J Trauma* 2004, 57(1 Suppl):S2-6). pGlcNAc patches, which contain microalgal nanofibers (SyvekPatch™, Marine Polymer Technologies, Danvers, Mass.), have been characterized as hemostatic agents to control bleeding following catheter removal, and are currently used in interventional cardiology and radiology as non-invasive closure devices. (Vournakis J N, Demcheva M, Whitson A, Guirca R, Pariser E R. Isolation, purification, and characterization of poly-N-acetyl glucosamine use as a hemostatic agent. *J. Trauma* 2004,57(1 Suppl):S2-6); (Najjar S F, Healey N A, Healey C M, McGarry T, Khan B, Thatte H S, et al. Evaluation of poly-N-acetyl glucosamine as a hemostatic agent in patients undergoing cardiac catheterization: a double-blind, randomized study. *J Trauma* 2004; 57(1 Suppl):S38-41).

The N-acetyl glucosamine-containing oligo- and polysaccharides are an important class of glycosaminoglycans, molecules largely represented in the dermis and have superior wound healing properties. They are already used for inhibition of surgical adhesions, relief from joint pain, and for skin replacement in reconstructive surgery. (Fazio V W, Cohen Z, Fleshman J W, van Goor H, Bauer J J, Wolff B G, et al. Reduction in adhesive small-bowel obstruction by Seprafilm adhesion barrier after intestinal resection. *Dis. Colon Rectum* 2006; 49(1):1-11); Pena Ede L, Sala S, Rovira J C, Schmidt R F, Belmonte C. Elastoviscous substances with analgesic effects on joint pain reduce stretch-activated ion channel activity in vitro. *Pain* 2002, 99(3):501-8); Orgill D P, Straus F H, 2nd, Lee R C. The use of collagen-GAG membranes in reconstructive surgery. *Ann N Y Acad. Sci.* 1999; 888:233-48; Pietramaggiori, G., Yang, H., Scherer, S. S., Kaipainen, A., Chan, R. K., Alperovich, M., Newalder, J., Demcheva, M., Vournakis, J. N., Valeri, R. C., Hechtman, H. B., Orgill, D. P. Effects of poly-N-acetyl glucosamine (pGlcNAc) patch on wound healing in db/db mouse. *J. Trauma* (2008) 64(3):803-808.; Vournakis, J., Eldridge, J., Demcheva M. and Muise-Helmericks, R. Poly-N-Acetyl Glucosamine Nanofibers Regulate Endothelial Cell Movement and Angiogenesis: Dependency on Integrin Activation of Etsl. *J. Vascular Res,* (2008) 45:222-232.)

In addition, N-acetyl glucosamine is contained in chitosan, a polymer with demonstrated hemostatic properties. (Malette W G, Quigley H J, Gaines R D, Johnson N D, Rainer W G. Chitosan: a new hemostatic. *Ann Thorac Surg* 1983, 36(1): 55-8). Although based on similar molecules, pGlcNAc and chitosan have structural, chemical, and biological differences; the former is constituted of highly ordered insoluble fibers, while the latter demonstrates a heterogeneous and soluble structure. (Fischer T H, Connolly R, Thatte H S, Schwaitzberg S S. Comparison of structural and hemostatic properties of the poly-N-acetyl glucosamine Syvek Patch with products containing chitosan. *Microsc Res Tech* 2004, 63(3):168-74). These structural dissimilarities result in hemostatic differences between the two materials. When compared, pGlcNAc patches induced hemostasis in 100% of cases, whereas several chitosan-based patches performed worse than a gauze pad control. (Fischer T H, Connolly R, Thatte H S, Schwaitzberg S S. Comparison of structural and hemostatic properties of the poly-N-acetyl glucosamine Syvek Patch with products containing chitosan. *Microsc Res Tech* 2004, 63(3):168-74).

Poly-N-acetyl glucosamine nanofibers interact with platelets, red blood cells and endothelial cells, (Thatte H S, Zagarins S, Khuri S F, Fischer T H. Mechanisms of poly-N-acetyl glucosamine polymer-mediated hemostasis: platelet interactions. *J Trauma* 2004; 57(1 Suppl):S13-21); (Thatte H S, Zagarins S E, Amiji M, Khuri S F. Poly-N-acetyl glucosamine-mediated red blood cell interactions. *J Trauma* 2004; 57(1 Suppl):S7-12) and accelerate hemostasis through a sequence of events that have been recently demonstrated. (Fischer T H, Thatte H S, Nichols T C, Bender-Neal D E, Bellinger A D, Vournakis J N. Synergistic platelet integrin signaling and factor XII activation in poly-N-acetyl glucosamine fiber-mediated hemostasis. *Biomaterials* 2005, 26(27):5433-43; Fischer, T. H., Valeri, C. R., Smith, C. J., Scull, C. M., Merricks, E. P., Nichols, T. P., Demcheva, M. and Vournakis, J. N. Non-classical Processes in Surface Hemostasis: Mechanisms for the Poly-N-acetyl glucosamine-induced Alteration of Red Blood Cell Morphology and Prothrombogenicity. (2008) *J. Biomedical Materials Res,* in press; Smith, C. J., Vournakis, J. N., Demcheva, M. and Fischer, T. H. Differential Effect of Materials for Surface Hemostasis on Red Blood Cell Morphology. (2008) *Microscopic Res. Techniques,* in press.)

Platelets specifically interact with the nanofibers of the pGlcNAc patch and, as a result, their activation is amplified. The activation response includes pseudopodia extension, shape change, integrin complex activation, activation of calcium signaling, phosphatidyl serine exposure on the surface membrane, binding of factor X to platelets and an acceleration of fibrin polymerization kinetics. Upon activation, platelets release vasoconstrictor substances and activate clotting after contact with the nanofibers, thus contributing to wound healing.

Therefore an appliance incorporating a hemostatic agent, preferably the hemostatic agent pGlcNac, that could be incorporated into a negative pressure wound care device such as the VAC would be highly desirable.

DESCRIPTION OF THE FIGURES

FIG. 2. shows a summary of the clinical observations of test animals of Example 1 indicating no signs of toxicity of the test articles.

FIG. 3 shows the results of a Macroscopic evaluation of the various test articles and controls articles implanted in Example 1.

FIGS. 4A-C shows the results of the microscopic evaluation of the test articles and the control articles of Example 1 for each of the three test animals used

FIG. 6 provides data from the wound epithelialisation study of Example 4.

FIG. 7 provides data from wound epithelialisation and wound contraction measurements of Example 4.

SUMMARY OF THE INVENTION

Figure 1:
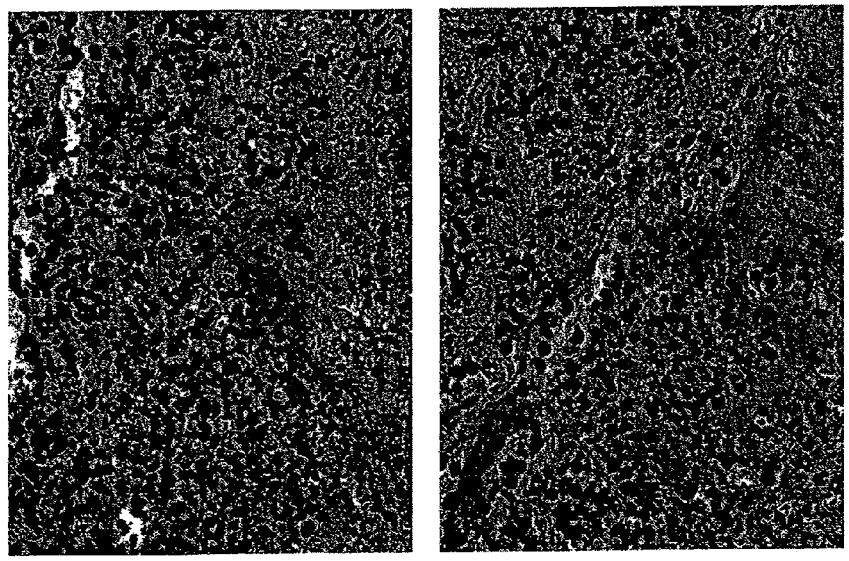
FIG. 1 shows wounds treated with pGlcNac and VAC technologies. 7 days post treatment wounds show high levels of proliferating cells contributing to wound healing (as shown by Ki-67 Immunohistochemical staining, a marker for actively proliferating cells).

The invention contemplates a wound healing appliance for use with a negative pressure comprising a support that promotes uniform distribution of pressure within the wound; and a hemostatic agent attached to the support. In one embodiment the support is a screen. In a further embodiment the support may be a foam. The hemostatic agent may be any known hemostatic agent including of fibrin, thrombin, oxidized regenerated cellulose, cryoprecipate, platelets and blood clotting cascade factors including Factor VII, VIII, IX.

In a preferred embodiment the hemostatic agent is collagen; In another preferred embodiment the haemostatic agent comprises poly-N-acetylglucosamine.

The invention also comprises a system for wound healing comprising (a) a system for delivering negative pressure to a wound and (b) a wound healing appliance comprising a screen or other open pore structure scaffold coated with a hemostatic agent. In one aspect of the invention the hemostatic agent is Poly-N-acetyl glucosamine nanofibers (pGlcNac). In one embodiment the wound healing appliance consists of an open pore polyurethane foam coated on its active surface with Poly-N-acetyl glucosamine nanofibers. In another embodiment the wound healing appliance is a pGlcNac coated screen.

In one aspect, the wound healing system of the invention comprises a wound healing appliance, such as pGlcNac coated screen or foam, an impermeable cover, a connecting tube, and a vacuum source.

In another aspect, the invention comprises a system that delivers sub-atmospheric pressure to the wound for the purpose of wound healing and hemostasis including: (a) a device that delivers a vacuum pressure in the range of 0 to 250 mm Hg; (b) a seal that is semipermeable that covers the wound;(c) a tube connecting the device to the seal; and (d) a wound healing appliance comprising (i)) a support that promotes uniform distribution of pressure within the wound; and (ii) a hemostatic agent attached to the screen.

In one embodiment the wound healing appliance comprises a hemostatic agent comprising poly-N-acelylglucosamine with a mean fiber size of about less than 10 microns. In a preferred embodiment the fiber size is from about 2 to about 4 microns. The thickness of the wound healing appliance will vary according to the application and the type of support used. In one embodiment a thin film of poly-N-acelylglucosamine would act as its own scaffold and be absorbed into the wound site. In a different embodiment the pGlcNac would be disposed over a wire mesh support.

In a further embodiment the pGlcNac would be disposed on or in a scaffold, preferably a porous scaffold such as a porous sponge that will allow cellular in-growth. The preparation of such porous sponges is well known in the art. Generally, the sponge would be prepared by lyophilization and would generally have a pore size of greater than 10 microns and less than 500 microns, preferably with pores in the range of 50-150 microns and most preferably with pore sizes about 100 microns.

In another embodiment, the hemostatic agent is composed of collagen with a mean fiber length of 0.01 to 5 microns in size. In a further embodiment, the hemostatic agent is composed of Type I collagen. In yet another embodiment, the hemostatic agent is composed of collagen that has been dispersed in a solution greater than pH 3.2. In yet another embodiment the hemostatic agent is composed of collagen that has a biodegradation time of 0.5 to 10 days. In yet another embodiment, the hemostatic agent is composed of collagen that has a thickness on the screen of 0.01 to 100 microns.

In a further aspect of the system of the invention can be comprised of a hemostatic agents comprised of a material selected from the group consisting of fibrin, thrombin, oxidized regenerated cellulose, chitin, chitosan, calcium alginate, cryoprecipate, platelets and blood clotting cascade factors including Factor VII, VIII, IX In another aspect the invention is system that delivers sub-atmospheric pressure to the wound for the purpose of wound healing and hemostasis that includes: a device that delivers a vacuum pressure in the range of 0 to 250 mm Hg; a seal that is semipermeable that covers the wound; a tube connecting the appliance to the seal; and an appliance wherein the appliance is hemostatic, improves wound healing and has a bioreactivity rating of less than 1.5. In a preferred embodiment the appliance has a bioreactivity of less than 1.0, more preferably less than 0.6, even more preferably less than 0.5 and most preferably about 0.0 or below when compared to high density polyethylene or other suitable controls.

The invention also comprises a method of treating a wound using the system(s) of the invention. In one aspect the invention is a method of treating a wound comprising providing a hemostatic appliance comprising a support that promotes uniform distribution of pressure within the wound and a hemostatic agent attached to the support, applying the hemostatic appliance to the wound so as to at least partially cover the wound and applying a vacuum pressure in the range of 0 to 250 mm Hg to the hemostatic appliance and the wound. In a preferred embodiment the hemostatic appliance is applied to the wound before the application of the vacuum or negative pressure to the appliance and the wound. In a more preferred embodiment the hemostatic appliance is applied at least 6 hours, at least 8 hours, at least 12 hours, at least 16 hours, at least 18 hours, at least 20 hour, at least 24 hours, at least 30 hours, at least 36 hours, at least 42 hours or at least 48 hours prior to the application of negative pressure to the wound and/or hemostatic appliance. In a most preferred embodiment the hemostatic appliance is applied to the wound about 24 hours before the application of negative pressure.

DETAILED DESCRIPTION OF THE INVENTION

Background

It has been previously shown that shown that, in VAC systems, a foam, or screen, interface is critical for transferring subatmospheric pressure to the wound because the system causes microdeformations of wound tissue only in areas of foam contact (FC). (Saxena V, Hwang C W, Huang S, Eichbaum Q, Ingber D, Orgill D P. Vacuum-assisted closure: microdeformations of wounds and cell proliferation. Plast Reconstr Surg. 2004; 114(5):1086-96; discussion 1097-8). Wound areas covered with just a polyurethane drape without foam contact (WFC), in contrast, do not develop microdeformations although these areas are presumably exposed to at least some of the vacuum pressure. In addition, unlike WFC tissue, FC areas show significant granulation tissue. (Orgill D P, Bayer L R, Neuwalder J, Felter R C. Global surgery—future directions. Microdeformational wound therapy-a new era in wound healing. Business Briefing. 2005:22-25).

Although the VAC system and other suction devices are referred to as negative pressure wound therapy (NPWT) or sub-atmospheric wound therapy (SAWT), we prefer the term microdeformational wound therapy (MDWT) because a properly designed foam is required to transmit microdeformations to the wound surface. Several mechanisms may explain how MDWT accelerates wound closure. First, because cell shape is known to be important for cell proliferation, tension caused by microdeformations in the wound may activate signal transduction and cell division. (Armstrong, D. G. & Lavery, L. A. Negative pressure wound therapy after partial diabetic foot amputation: a multicentre, randomised controlled trial. *Lancet* 366, 1704-10 2005); (Saxena, V. et al. Vacuum-assisted closure: microdeformations of wounds and cell proliferation. *Plast Reconstr Surg* 114, 1086-96; discussion 1097-8 2004); (Ulbrecht, J. S., Cavanagh, P. R. & Caputo, G. M. Foot problems in diabetes: an overview. *Clin Infect Dis* 39 Suppl 2, S73-82 2004); (Vournakis, J. N., Demcheva, M., Whitson, A., Guirca, R. & Pariser, E. R. Isolation, purification, and characterization of poly-N- acetyl glucosamine use as a hemostatic agent. *J Trauma* 57, S2-6 2004). Second, blood flow has been shown to increase as a result of MDWT in animals, although this has not been studied in humans. (Najjar, S. F. et al. Evaluation of poly-N-acetyl glucosamine as a hemostatic agent in patients undergoing cardiac catheterization: a double-blind, randomized study. *J Trauma* 57, S38-41 2004). Finally, the open pore foam may facilitate the removal of excess wound exudates, thus liminating harmful enzymes and improving nutrient diffusion.

Device

The invention contemplates a wound healing appliance comprising a scaffold comprising a screen or other open pore structure device coated with a hemostatic agent. In one aspect of the invention the scaffold is coated with Poly-N-acetyl glucosamine nanofibers (pGlcNac). In a preferred embodiment the appliance consists of an open pore polyurethane foam coated on its active surface with Poly-N-acetyl glucosamine nanofibers. The method of coating could include evaporation, lyophilization, casting or spraying.

Parameters that can be optimized during manufacture include the nature and concentration of various solvents, the thickness of the coating mechanism, the characteristics of the fibers (if any) of the hemostatic appliance coating, as well as the pH under which the device is manufactured.

The invention also contemplates a wound healing system consisting of a pGlcNac screen, an impermeable cover, a connecting tube, and a vacuum source.

In this invention the hemostatic or clotting agents can be used in sequence or as an integrated part of the scaffold. For example, in one example pGlcNac fibers were sprayed on traditional gauze wraps to attain hemostasis within a wound, prior to re-applying negative pressure wound therapy. More convenient to the surgeon, however would be to have the VAC device fabricated with the hemostatic agent already placed. Methods of fabrication are discussed below.

Methods of Manufacture

One would appreciate that there are a number of different methods for manufacturing the hemostatic appliance of the invention. In particular, the appliance of the invention is comprised of an open cell or pore structure device coated or otherwise fabricated with a hemostatic agent. Preferably, the hemostatic agent is pGlcNac Methods include coating a support such a foam or a screen with the hemostatic agent by spraying or painting the agent on the support. Other fabrication methods can incorporate such techniques as microfabrication, lyophilization, the addition of the hemostatic agent with a microcarrier and nano-technology techniques.

EXAMPLES

Numerous embodiments of the system and the device of the invention are contemplated. These include but are not limited to the device and systems shown in the examples below:

Example 1

Biocompatability of Sample Implant

The purpose of the study was to evaluate the test article for the potential to induce local toxic effects after implantation in the muscle tissue of albino rabbits. The test article, MP719, (2-4 micron poly-N-acetyl glucosamine nanofibers; Marine Polymer Technologies, Inc., Danvers, Mass.), was implanted in the paravertebral muscle tissue of New Zealand White rabbits for a period of 4 weeks. The test article was evaluated separately using two control articles, Sponsor-specified Surgicel and Negative Control High Density Polyethylene (Negative Control Plastic). The results indicated that the test article was non-reactive when implanted for 4 weeks (Bioreactivity Rating of 0.2) when compared to Surgicel; and non-reactive (Bioreactivity Rating of 0.0) when compared to Negative Control High Density Polyethylene (Negative Control Plastic)

The study was conducted based upon the following references: ISO 10993-6, 1994, Biological Evaluation of Medical Devices—Part 6: Tests for Local Effects After Implantation; ISO 10993-12, 2002, Biological Evaluation of Medical Devices—Part 12: Sample Preparation and Reference Materials; ASTM F981-04, Standard Practice for Assessment of Compatibility of Biomaterials for Surgical Implants with Respect to Effect of Materials on Muscle and Bone, 2004; 2.4 ASTM F763-04, Standard Practice for Short Term Screening of Implant Materials, 2004; 2.5 ISO/IEC 17025, 2005, General Requirements for the Competence of Testing and Calibration Laboratories Methods and Materials Three healthy New Zealand white rabbits (*Oryctolagus cuniculus*) 2 males and 1 female with a weight/age Range: 2.93-3.18 kilograms/at least 12 weeks old (adult) were used in the study Albino rabbits were used in this study because they have historically been used in safety evaluation studies and the guidelines have no alternative (non-animal) methods. The species, number of animals, as well as the route of administration used, are recommended by the ISO 10993-6 guidelines.

The test article (MP719) measured approximately 1 mm to in width and 10 mm in length and was sterile. The two control articles were prepared. The first control, Surgicel (C1), measured approximately 1 mm in width by 10 mm in length and was received sterile. The second control, Negative Control Plastic (C2), measured approximately 1 mm in width by 10 mm in length and was sterilized by dipping in 70% ethanol.

Each animal was weighed prior to implantation. On the day of the test, the dorsal side of the animals were clipped free of fur and loose hair was removed by means of a vacuum. Each animal was appropriately anesthetized. Prior to implantation, the area was swabbed with a surgical preparation solution. Four test article strips were surgically implanted into each of the paravertebral muscles of each rabbit, approximately 2.5 cm from the midline and parallel to the spinal column and approximately 2.5 cm from each other. The test article strips were implanted on one side of the spine. In a similar fashion, control article strips (C1—Surgicel) were implanted in the contralateral muscle of each animal. Two control strips (C2—Negative Control Plastic) were implanted caudal (toward the tail) to the test article and to C1 control implant sites on either side of the spine (total of four strips). A total of at least eight test article strips and eight of each control article strips are required for evaluation.

The animals were maintained for a period of 4 weeks. The animals were observed daily for this period to ensure proper healing of the implant sites and for clinical signs of toxicity. Observations included all clinical manifestations. At the end of the observation period, the animals were weighed. Each animal was sacrificed by an injectable barbiturate. Sufficient time was allowed to elapse for the tissue to be cut without bleeding.

The paravertebral muscles in which the test or control articles were implanted were excised in tow from each animal. The muscle tissue was removed by carefully slicing around the implant sites with a scalpel and lifting out the tissue. The excised implant tissues were examined grossly, but without using excessive invasive procedures that might have disrupted the integrity of this tissue for histopathological evaluation. The tissues were placed in properly labeled containers containing 10% neutral buffered formalin. Following fixation in formalin, each of the implant sites was excised from the larger mass of tissue. The implant site, containing the implanted material, was examined macroscopically. Each site was examined for signs of inflammation, encapsulation, hemorrhaging, necrosis, and discoloration using the following scale: 0=Normal; 1=Mild; 2=Moderate; 3=Marked.

After macroscopic observation, the implant material was left in-situ and a slice of tissue containing the implant site was processed. Histologic slides of hematoxylin and eosin stained sections were prepared The following categories of biological reaction were assessed by microscopic observation for each implant site:
1. Inflammatory Responses:
a. Polymorphonuclear leukocytes
b. Lymphocytes
c. Eosinophils
d. Plasma cells
e. Macrophages
f. Giant cells
g. Necrosis
h. Degeneration
2. Healing Responses:
a. Fibrosis
b. Fatty Infiltrate Each category of response was graded using the following scale: 0=Normal; 0.5=Very Slight; 1=Mild; 2=Moderate; 3=Marked. The relative size of the involved area was scored by assessing the width of the area from the implant/tissue interface to unaffected areas which have the characteristics of normal tissue and normal vascularity. Relative size of the involved area was scored using the following scale:
0=0 mm, No site
0.5=up to 0.5 mm, Very slight
1=0.6-1.0 mm, Mild
2=1.1-2.0 mm, Moderate
3=>2.0 mm, Marked For each implanted site, a total score is determined. The average score of the test sites for each animal is compared to the average score of the control sites for that animal. The average difference between test and controls for all animals is calculated and the initial Bioreactivity Rating is assigned as follows:
0-1.5 No Reaction*
>1.5-3.5 Mild Reaction
>3.5-6.0 Moderate Reaction
>6.0 Marked Reaction
* A negative calculation was reported as zero (0).

The pathology observer reviews the calculated level of bioreactivity. Based on the observation of all factors (e.g. relative size, pattern of response, inflammatory vs. resolution), the pathology observer revised the Bioreactivity Rating.

A descriptive narrative report regarding the biocompatibility of the test material is provided by the pathology observer. The study and its design employ methodology to minimize uncertainty of measurement and control of bias for data collection and analysis
Results All three of the test animals increased in weight. None of the test animals exhibited any signs of toxicity over the course of the study. Clinical Observations (FIG. 2, Table I).

Macroscopic evaluation of the test article and control implant sites indicated no significant signs of inflammation, encapsulation, hemorrhage, necrosis, or discoloration at the 4 week time period. Some test sites and the majority of the Surgicel control, were not seen macroscopically and serial sections were submitted for microscopic evaluation. (FIG. 3, Table II).

Microscopic evaluation of the test article implant sites indicated no significant signs of inflammation, fibrosis, hemorrhage, necrosis, or degeneration as compared to each of the control article sites. The Bioreactivity Rating for the 4 week time period (average of three animals) was 0.2, (C1—Surgicel) and 0.0 (C2—Negative Control Plastic) indicating no reaction as compared to either of the control implant sites. The pathologist noted there was a moderate polymorphic and histiocytic (macrophages) infiltrate around the in situ test article that was not unexpected given the nature of the test material (FIGS. 4A-C, Table III).

Example 2

Diabetic Mouse—Granulation Tissue Measurements

Homozygous, genetically diabetic 8-12 week-old, Lep/r-db/db male mice (strain C57BL/KsJ-Lepr$^{db}$) were caged separately. Food and water were given ad libitum under an approved animal protocol in an AAALAC accredited facility. One day prior to surgery, dorsal hair was clipped and depilated (Nair®, Church & Dwight Co., Princeton, N.J.). Animals were weighed and anesthetized with 60 mg/kg Nembutal (Pentobarbital) prior to surgery. The dorsum was disinfected with 70% alcohol and a 1.0 cm$^2$ area of skin and panniculus carnosus was excised creating a full-thickness dorsal excisional wound. Wounds edges were protected with a 0.5 cm wide and 0.2 cm thick DuoDERM® (DuoDERM®, CGF®, ConvaTec, Squibb & Sons, L.L.C.) frame and dressing changes were performed on days 2 and 4. On day 7, animals were euthanized, and the wound area with its surrounding skin and underlying tissue was excised en block. The other half was fixed en block in 10% neutral-buffered formalin solution and kept in 70% alcohol at 4° C. until paraffin embedment.
Study Groups Three animals were used in each study group. Granulation tissue responses were compared of wounds treated with:
1. Occlusive dressing (DuoDERM® frame) alone,
2. Complete VAC system (V.A.C., KCI, San Antonio, Tex., 125 mm Hg suction),
3. Surgicel (Ethicon Inc., Somerville, N.J.),
4. MP719 (2-4 micron poly-N-acetyl glucosamine nanofibers; Marine Polymer Technologies, Inc., Danvers, Mass.),
5. MP719+VAC (125 mm Hg suction)
Granulation Tissue Measurement Paraffin embedded tissues were sectioned and stained according to routine Hematoxylin and Eosin (H&E) protocols. Panoramic sectional digital images of each H&E stained cross section wound were prepared using Adobe Photoshop CS Software (Adobe Systems Incorporated, San Jose, Calif.) to analyze granulation tissue area and thickness, using digital planimetry (Image J, NIH, Bethesda, Md.) by two independent observers, blinded to the treatment, to quantify the area of granulation tissue in the middle part of each section at 10× magnification.
Results Data are shown in Table A below. The experimental groups, listed above, are compared to the Occlusive Dressing (OD) control. The data clearly show that the combination of MP719 and VAC provides an increase in the granulation tissue on day 7 of a wound healing study in the diabetic mouse animal model system. The combination of poly-N-acetyl glucosamine nanofibers plus VAC results in a greater than doubling of the granulation tissue generated at day 7. This is a strong indicator that the VAC—poly-N-acetyl glucosamine nanofibers combination provides a synergistic effect.

TABLE A

Comparative Granulation Tissue Area (Day 7 data)

| Sample | Number of Mice | % Granulation Tissue |
| --- | --- | --- |
| OD | 3 | 100 |
| VAC | 3 | 140 |
| Surgicel | 3 | 90 |
| MP719 | 3 | 160 |
| MP719 + VAC | 3 | 330 |

Example 3

Hemostatic Effect & Synergy with Negative Pressure

A 63-year-old female with hypertension, type 2 diabetes, and end-stage renal failure requiring dialysis (BMI 300 pounds and measuring 5 feet 4 inches) presented with a large mass along the lateral region of her left hip and thigh. Diagnosis at that time was undifferentiated sarcoma involving the left lateral soft tissues from the pelvis caudad to the iliac crest up to the distal one third of the thigh. The selected course of treatment involved external beam radiation followed by surgical resection.

Administering radiation therapy prior to surgical resection provides several potential benefits including reduced tumor volume and seeding during surgical manipulation and improved overall survival. However, the incidence of wound complications has been reported to be two-fold higher after preoperative compared with postoperative radiation therapy and such complications have been shown to have detrimental effects on patient function. Current guidelines from the National Comprehensive Cancer Network recommend an interval of 3 to 6 weeks between the end of preoperative radiation therapy and surgical resection to minimize risk of wound complications.

During the fifth week of radiation therapy severe bleeding from the sarcoma resulted in hemoglobin decrease to 5 gm/L. Radiation therapy was continued for the recommended total of 50.4 gray (Gy) over 5 weeks to complete the treatment cycle with the goal of ameliorating the bleeding. However, the patient had two additional bleeding episodes during the last week of radiation, each to the same low level of hemoglobin.

A CT scan of the thigh on showed multiple large vessels feeding the tumor along its entire base. Due to the uncontrolled bleeding and the patient's multiple co-morbidities, the multidiscipline medical team and the patient agreed to proceed with surgical resection at this time rather than wait the customary 3 to 6 weeks after radiation.

Surgical resection of an extremity soft tissue sarcoma immediately post radiation therapy is undesirable due to increased risk of thrombosis, bleeding, and complications of wound healing.

During end-block resection of the sarcoma and superficial groin dissection, prolific bleeding arose from the resection basin. The placement of 6 poly-N-Acteyl Glucosamine (pGlcNAc) hemostat pads along the resection basin between the left hip and thigh with pressure applied for 5 minutes brought immediate hemostasis to the surgical field.

The postsurgery wound was treated with negative pressure wound therapy (V.A.C.®, Kinetic Concepts Inc., San Antonio, Tex.).

The combination of the pGlcNAc hemostatic pad and V.A.C. allowed for immediate application of the V.A.C. post surgically. The wound interface coated with pGlcNAc resulted in increased granulation tissue and accelerated preparation of the wound for a skin graft.

Example 4

Optimizing Combination of VAC and Short Poly-N-acetyl glucosamine (sNAG) Fibers

Short fiber poly-N-acetyl glucosamine nanofibers (sNAG), are effective haemostatic agents that activate platelets and facilitate wound epithelialization. We hypothesized that sNAG used in combination with the VAC device could be synergistic in promoting wound healing while minimizing the risk of bleeding.

Membranes consisting of sNAG were applied immediately to dorsal excisional wounds of db/db mice followed by application of the VAC device. Wound healing kinetics, angiogenesis and wound related growth factor expression were measured.

The application of sNAG membranes to wounds 24 hours prior application of the VAC device was associated with a significant activation of wounds (expression of PDGF, TGFβ, EGF), superior granulation tissue formation rich in Collagen I as well as superior wound epithelialisation (8.6±0.3 vs 1.8±1.1% of initial wound size, p<0.05) and wound contraction.

The application of sNAG membranes prior to the application of the polyurethane foam interface of VAC devices leads to superior healing, and represents a promising wound healing adjunct that can also reduce the risk of bleeding complications.

Engineering of pGlcNAc (sNAG) Membranes

Gamma irradiated native diatom-derived pGlcNAc (Marine Polymer Technologies, Inc, Danver, Mass.) nanofibers (sNAG) with an average length of 4-7 µm, width of 100-150 nm and thickness of 40-60 nm were formulated into membranes. The sNAG membranes were prepared by filtration and drying procedures, and consisted entirely of the sNAG nanofibers with no additional components. The thin (0.3 mm) sNAG membranes were produced by filtration and drying suspensions of the sNAG nanofibers. The materials were free of proteins, metal ions, and other contaminants.

Wound Healing Model

Homozygous, genetically diabetic 10 week-old, Lep/r-db/db male mice (strain C57BL/KsJLepr db, Jackson Laboratory, Bar Harbor, Me.) were used under an approved animal protocol in an AAALAC accredited facility. Twenty-four hours prior to surgery, the entire back of the animals was clipped and depilated (Nair®, Church & Dwight Co., Princeton, N.J.). Animals were anesthetized with 60 mg/kg Nembutal (Pentobarbital) 15 minutes prior to surgery. After disinfecting the dorsum with alcohol patches, a 1.0 cm$^2$ area of skin and panniculus carnosus were removed to create a full-thickness wound. Excessive wound margins deformation was prevented with a 0.5 cm wide Duoderm® (DuoDERM®, CGF®, ConvaTec, Squibb & Sons, L.L.C.) frame placed around the wound edges. Wounds were covered with semi-occlusive polyurethane dressings (Tegaderm™, 3M, St. Paul, Minn.) and the VAC device was applied either directly after wounding or 24 hours after wounding depending on the study group. The VAC dressing was changed on day 4. After 6 days of VAC treatment, the VAC dressing was removed and wounds were treated twice a week with an occlusive Tegaderm dressing until day 21, when animals were anesthestized with Isofluran inhalation (Isoflurane, USP, NOVAPLUS, Lake Forest, Ill., USA). The cranial wound half was used for western blot and RT-PCR analysis, wound cross-sections were harvested from the distal wound half including surrounding skin and underlying muscle tissue, formalin fixed and embedded in paraffin.

Study Groups

Figure 5:
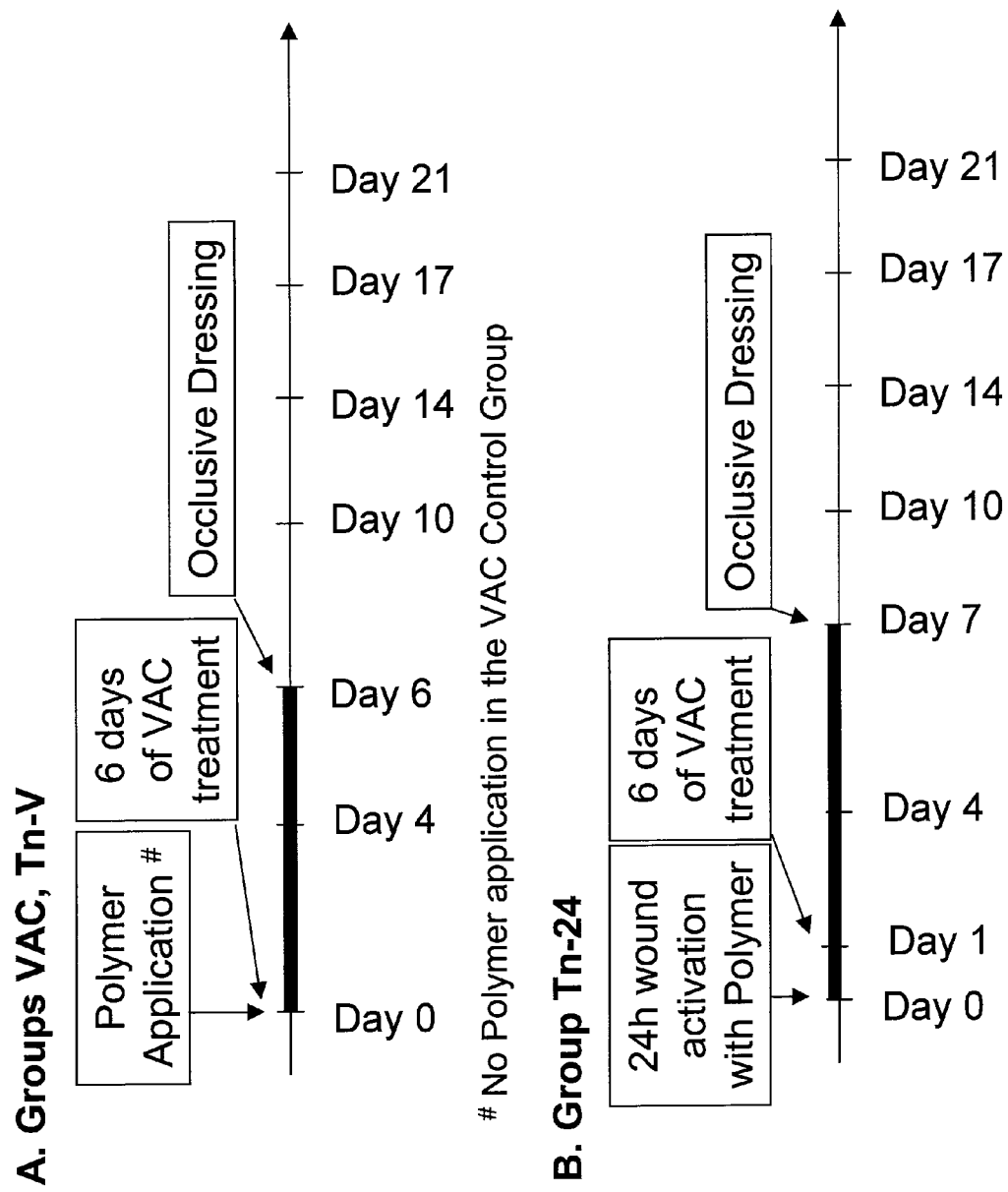
FIG. 5 illustrates the study design of in Example 4.

In order to determine the optimal combination of sNAG membranes and VAC polyurethane foam dressing, the following groups were compared in regard of wound healing and expression of wound healing related growth factors. Wounds treated by VAC polyurethane foam dressing only (without sNAG membranes) were used as controls (VAC Group) and were treated with 6 days of VAC followed by occlusive dressing treatment until day 21, when animals were sacrificed. Dressing changes were performed twice a week as described in FIG. 1. VAC dressing included a semiocclusive adhesive covering (KCI drape; Kinetic Concepts Inc.), a polyurethane foam (Granulofoam™, Kinetic Concepts Inc.), a flexible tube which allows undisturbed activity of the treated animals and is composed of two separated tubes of 1 mm diameter as well as a suction device set at 125 mmHg negative pressure (KCI Pump; Kinetic Concepts Inc.). The study groups were as follows: (1) VAC control group—wounds treated by VAC polyurethane foam dressing only. Treatment with VAC was for 6 days followed by occlusive dressing treatment until day 21, when animals were sacrificed; (2) Tn-24—wounds with treated with a 1×1 cm thin (0.3 mm thickness) sNAG membrane moistened with one drop of sterile saline solution for 24 hours followed by VAC treatment as above;and (3) Tn-V—wounds were treated with a 1×1 cm thin (0.3 mm) sNAG membrane moistened with one drop of sterile saline solution and co-incident VAC treatment as above. The study groups and study plan are illustrated in FIG. 5.

Wound Closure Analysis

Wounds were photographed immediately after wounding, at each dressing change, and at harvest time. Digital photographs captured at the end of the experiment were compared with initial photographs. Wound contraction and wound epithelialization were measured by digital planimetry (Image J, NIH, Bethesda, Md.). The experiment was stopped by an independent observer blinded to the treatment mode at day 21, when the first of the analyzed groups achieved complete healing.

Paraffin embedded tissues were sectioned and stained according to routine Hematoxylin and Eosin (H&E) protocols. Panoramic sectional digital images of 10× magnified H&E stained wound cross sections were prepared using Adobe Photoshop CS Software (Adobe Systems Incorporated, San Jose, Calif.). Granulation tissue thickness (FIG. 7B), wound contraction defect (FIG. 7C) and wound epithelialisation defect (FIG. 3a) were measured by digital planimetry (Image J, 7 NTH, Bethesda, Md.). The wound contraction defect corresponded to the distance measured between the margin of the subcutaneous adipose tissue of each wound side. The wound epithelialisation defect corresponded to the distance measured between newly built epithelium of each wound side. Results are expressed as the average of measurements performed by three independent observers, blinded to the treatment mode.

Immunohistochemistry for PECAM-1, Ki67

Analysis of wound bed vasculature and cellular proliferation was performed by immunohistochemistry. Central wound cross-sections, surrounding skin and underlying muscle tissue were harvested, formalin fixed and embedded in paraffin. Paraffin-embedded sections were re-hydrated through a decreasing alcohol chain. Antigen retrieval of CD31 was performed with 40 µg/ml Proteinase K (Roche Diagnostic Corp., Indianapolis, Ind.) solution in 0.2M Tris-H2O for 20 minutes at 37° C. After application of blocking serum for 1 hour, primary antibodies, namely CD31 (Pharmingen, San Jose, Calif.) for angiogenesis and Ki67 (LabVision, Freemont, Calif.) for cellular proliferation, slides were incubated at 4° C. overnight. Biotinylated mouse anti-rat secondary antibodies (Vector Laboratories Inc., Burlingame, Calif.) for CD-31 and peroxidase secondary rat anti-mouse (Labvision Corporation, Fremont, Calif.) were used as secondary antibodies. For CD31, signals were then amplified in association with Tyramide Amplification System® (Perkinelmer, Boston, Mass.). Activation was performed with NovaRED (Vector Laboratories, Burlingame, Calif.). Sections were then counterstained with hematoxilin (Hematoxilin 1, Richard-Allan Scientific, Kalamazoo, Mich.). High power images of stained sections were used to quantify the degree of wound bed angiogenesis and cellular proliferation. Six digital images of CD-31 stained slides were captured for each sample, 2 in the middle and two on each edge of the wound bed. Blood vessel density was quantified over the entire image and expressed as the ratio of blood vessel number per high-powered field (hpf). Cellular proliferation was quantified over the entire image and expressed as the ratio of Ki67 positive cells to the total number of nuclei. Ratios were calculated between results obtained from the different wound locations. A total of 36 microscopic fields were evaluated for each experimental group. Central wound cross-sections were stained according to routine H&E protocols.

Real-Time RT-PCR

Quantitative real-time RT-PCR expression of platelet derived growth factor BB chain (PDGF; Gene Bank ID AF162784; 5'-TGTTCCAGATCTCGCGGAAC-3'; 5'-GCG-GCCACACCAGGAAG-3'; Gene Bank ID AF162784), epidermal growth factor (EGF; Gene Bank ID NM_010113; 5'-CCAAACGCCGAAGACTTATCC-3'; 5'-TGATCCT-CAAACACGGCTAGAGA-3') and transforming growth factor beta 1 (TGF-β1; Gene Bank ID NM_011577; 5'-CAC-CATCCATGACATGAACC-3'; TCATGTTGGACAACTGCTCC-3') was performed and compared within groups using 28S ribosomal RNA (28S; Gene Bank ID X00525; 5'-TTGAAAATCCGGGGGAGAG-3'; 5'-ACATTGTTCCAACATGCCAG-3') as the endogenous control. At days 21 fresh samples were taken from the wound bed of the treated mice (n=3 per group) and fresh frozen. RNA was extracted using the RNeasy mini kit (Qiagen, Chatsworth, Calif.) and quantification performed using the NanoDrop (NanoDrop Technologies, Wilmington, Del.) method. SuperScript III First-Strand Synthesis System for RT-PCR (Invitrogen Life Technologies, Carlsbad, Calif.) was used to synthesize complementary deoxyribonucleic acid (cDNA). Total RNA was mixed with random hexamers and dNTP and then incubated. RT buffer, $MgCl_2$, DTT, RNaseOUT and SuperScript III RT were added, incubated and cooled. Then, E. coli RNase H was added and incubated. RT-PCR was performed in an ABI Prism 7300 system (Applied Biosystems, Foster City, Calif.) using $RT^2$ SYBR Green/ROX qPCR (SA Biosciences, Frederick, Md.). Amplification of the cDNA was performed in triplicates and a dissociation curve was generated utilizing fluorescence measurements with for normalization. Change in expression was considered significant when the baseline relative quantity (RQ) minimum/maximum values did not overlap with the sample RQ values at the 95% confidence interval determination.

Western Blot Analysis

At day 21 tissue was harvested from the wound bed and fresh frozen for western blot analysis of PDGF and Collagen I (n=3 per group). The samples were loaded on 15% SDS-polyacrylamide gel and run at 120V for 90 min. The protein was transferred to PVDF membrane and subsequently blocked for 2 h with 10% milk in TBST (10 mM Tris base pH 7.5, 150 mM NaCl, 0.1% Tween-20). The membrane was then incubated in primary polyclonal antibody against PDGF and Collagen I. Following three washes with TBST for 10 min each, the membrane was placed in the secondary goat-anti-rabbit antibody (Rockland Immunochemicals Inc., Gilbertsville, Pa., USA) for 1 hour. The enhanced chemiluminescence reaction (ECL, Amersham Biosciences, Iscataway, N.J., USA) was then carried out according to the manufacturer's instructions and films were developed for 30 seconds with phosphatase-conjugated secondary antibody.

Data Analysis

For comparison of two groups, a two-tailed T-test was used. For greater than two groups, one-way analysis of variance (ANOVA) and ad hoc Fischer's LSD tests was used to determine the significant differences between treatment groups if the ANOVA was found to be significant. All statistical analyses were performed using WinStat (R. Fitch Software, Lehigh Valley, Pa.). A p-value less than 0.05 was considered statistically significant.

Results

In order to evaluate wound epithelialization and wound contraction digital planimetry of dorsal wound pictures taken at each dressing change was done and compared among groups over time. The results, shown in FIG. 6, were analyzed by planimetric measurements of histological wound cross sections taken from the centre of the wound as described above. Wounds treated with a single application of sNAG membrane for 24 hours followed by the application of a VAC device (study group Tn-24) showed a significantly improved wound epithelialization in both dorsal wound pictures and histological wound cross sections. Treatment with the thin sNAG membranes for 24 hours prior to initiation of the VAC was able to achieve a more rapid wound closure. While at day 14, the VAC-only control wounds measured 68% of the initial wound size, the sNAG activated wounds were 87% epithelialized, corresponding to a 5 day acceleration in wound closure. The experiment was terminated by an independent observer blinded to the treatment mode at day 21, when the group treated with 24 hours activation with thin sNAG achieved complete healing. Comparable trends were found for wound contraction measurements, although these were less marked than wound epithelialisation measurements, as seen in FIG. 7.

A. Wound Activation for 24 Hours by sNAG Leads to Improved Granulation Tissue Formation at Day 21.

Granulation tissue formation is an important feature of wound healing and is often impaired in diabetic wounds. Wounds treated with sNAG nanofibers, Tn-24 and Tn-V, showed a trend towards increased granulation tissue formation when compared to the VAC-only control group (FIG. 8C). No difference was found between wounds which had a 24 hour wound activation with the sNAG nanofibers (Tn-24) prior to application of the VAC dressing, and wounds where sNAG and VAC were applied jointly without a time delay (Tn-V).

In order to assess the quality of the newly generated granulation tissue, protein levels of Collagen I were measured by western blot analysis in tissues harvested from the wound bed (FIG. 8A). Collagen I levels were significantly increased in wounds treated with sNAG for both groups Tn-V and Tn-24 (Relative Intensity of Western Blot Bands: Tn-V=0.7 vs Tn-24=0.9 vs. VAC=0.1; $p<0.01$ vs VAC).

B. Twenty Four Hour Wound Activation with sNAG Increases Growth Factor Release

To test the effect of sNAG on the expression and production of wound healing related growth factors, quantitative RT-PCR and western blot analysis of tissues harvested from the wound bed were performed. At 21 days after wounding protein levels of PDGF were higher in animals which had a 24 hours activation with sNAG fibers (FIG. 8A; Relative Intensity of Western Blot Bands: Tn-24=1.1 vs VAC=0.01; $p<0.01$). mRNA expression of PDGF measured in the same samples revealed already suppressed levels compared with the other groups analyzed (FIG. 8B; PDGF Tn-24 1±0.1 vs. Tn-V 5.6±1.7 vs. VAC 5.6±1.0, $p<0.01$). Comparable trends were observed in the mRNA expression levels of TGF-β (FIG. 9) with already suppressed levels in wounds treated with a 24 h activation with sNAG compared to wounds treated with a simultaneous application of sNAG and VAC as well as compared to VAC-only control group ($p<0.01$). EGF expression (FIG. 6) was reduced in wounds treated with sNAG and VAC (Tn-24 and Tn-V) compared to wounds treated with compared to VAC-only control wounds (EGF; Tn-24 1±0.6 vs. VAC 4.7±3.0, $p<0.01$; Tn-V 1.3±0.4 vs. VAC 4.7±3, $p<0.01$).

C. Twenty One Days After Treatment the Amount of Granulation Tissue Vessels and Proliferating Cells is Comparable Among Groups Histological wound cross sections stained with PECAM-1 and Ki67 were photographed and analysed for vessel density and cellular proliferation. 21 days after wounding animals of the 6 analyzed groups presented with comparable levels of vessels and proliferating cells. Because animals were harvested at day 21 only, no data is available about intermediate time points when possible differences among groups could have been present. This is however not to exclude as it is known that following a period of robust angiogenesis, wounds are characterized by a period of vascular regression D. Detailed Description of Experimental Data FIG. 5 shows the study groups and study design. FIG. 2A is a time chart of study design for VAC group, and the sNAG-VAC Group (Tn-V) where sNAG was applied and VAC was initiated immediately. In the Tn-V group sNAG membranes are changed at day 4. After a 6 days treatment, wounds are covered by occlusive dressings until day 21 and dressing changes are performed at day 10, 14 and 17. B. Time chart of study design for sNAG Group (Tn-24) where sNAG is applied for 24 hours prior to the initiation of the VAC. After a 24 hours the VAC was applied for 6 days and followed by an occlusive dressing treatment.

FIG. 6 shows the results of the Wound epithelialisation studies. A 24 hour activation with a sNAG membrane was associated with a more rapid wound epithelialisation and wound contraction. Approximately 90% wound closure was achieved by day 20 in the VAC-only control group and by day 15 in the sNAG 24 h activation group (Tn-24). * $p<0.05$ vs. VAC Group.

FIG. 7 provides the data from the wound epithelialization and wound contraction measurements FIG. 7A. is a wound cross section of Group Tn-24 treated mice (24 activation with sNAG prior VAC application for 6 days). The wound epithelialisation defect was measured by digital planimetry of central wound cross sections by measuring the distance between epidermal epithelialisation margins of both wound sides. Wound contraction was measured as the distance between the subcutaneous adipose tissue of both wound sides. Granulation tissue thickness was measured as the distance from the wound bed to the wound surface at the centre of the wound. FIG. 7B. is a wound contraction defect measurements of the analysed groups. FIG. 7C. is a wound epithelialisation measurements of the analysed groups. The Tn-24 group shows superior wound epithelialisation and wound contraction when compared with the other analyzed groups. * $p<0.05$ between Tn-24 Group and other groups. * $p<0.05$ vs. VAC Group.

Figure 8:
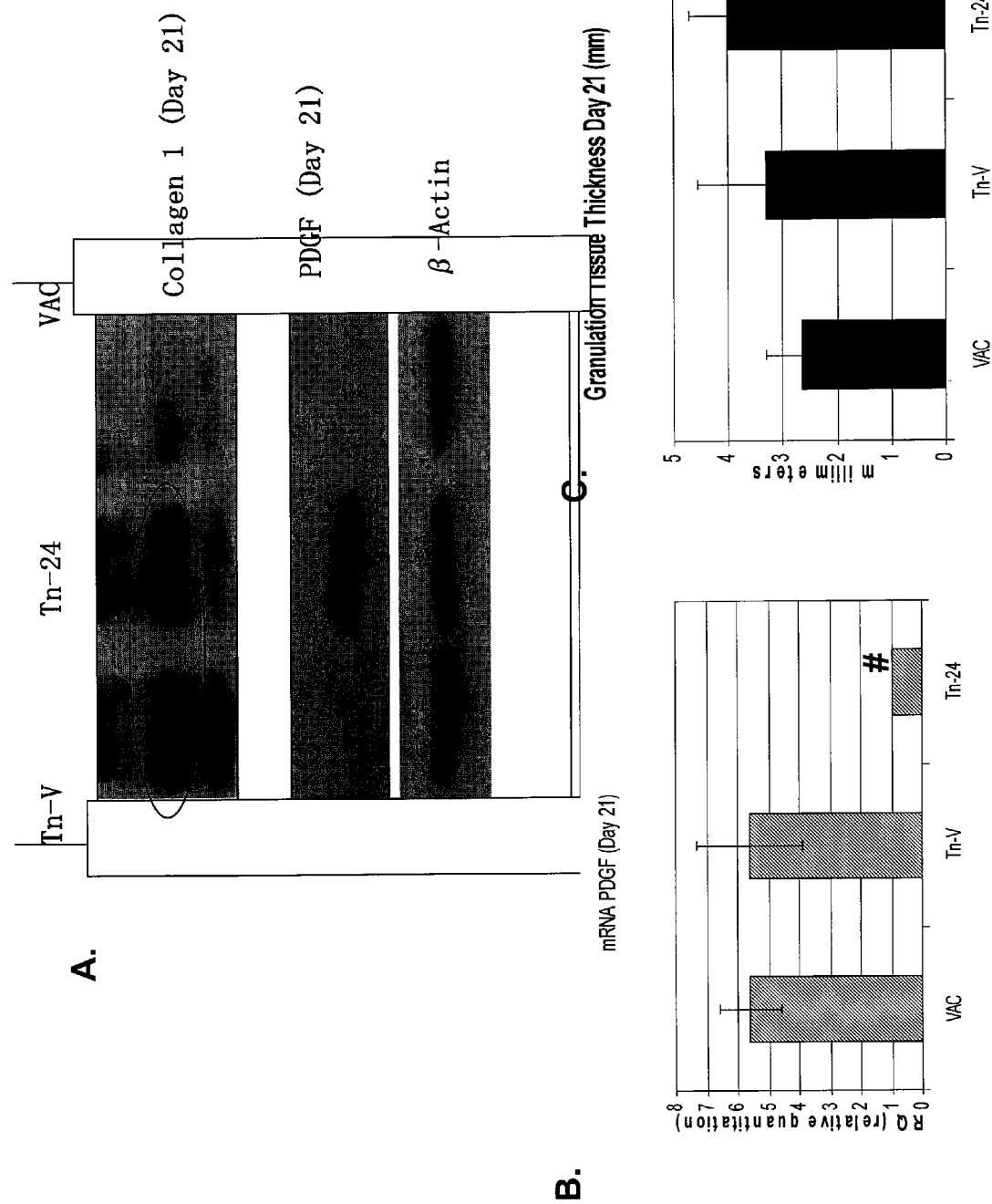
FIG. 8 illustrates the analysis of the granulation tissue in the treated groups of Example 4.

FIG. 8. is an analysis of the granulation tissue in the treated groups. FIG. 8A shows protein levels of Collagen 1 and PDGF assessed by western blot analysis in the granulation tissue of wounds treated by either VAC only, 24 h activation with sNAG followed by VAC (Tn-24), VAC and sNAG jointly (Tn-V). PDGF protein levels are higher in the Tn-24 group. The sNAG membrane induced increased protein levels of Collagen I irrespective of the application mode. FIG. 8B. shows the mRNA expression levels of PDGF in the analysed groups shows suppressed PDGF levels in the group which had a 24 hours wound activation ($p<0.05$). The higher PDGF protein levels in the Tn-24 group suggests earlier wound activation and release of wound healing related growth factors induced by the 24 h activation with the sNAG membrane. FIG. 8C. shows the granulation tissue measurements revealed superior granulation tissue formation in the Tn-24 Group when compared with the control Group (VAC). *<0.05 vs. VAC Group, #<0.01 vs VAC Group.

Figure 9:
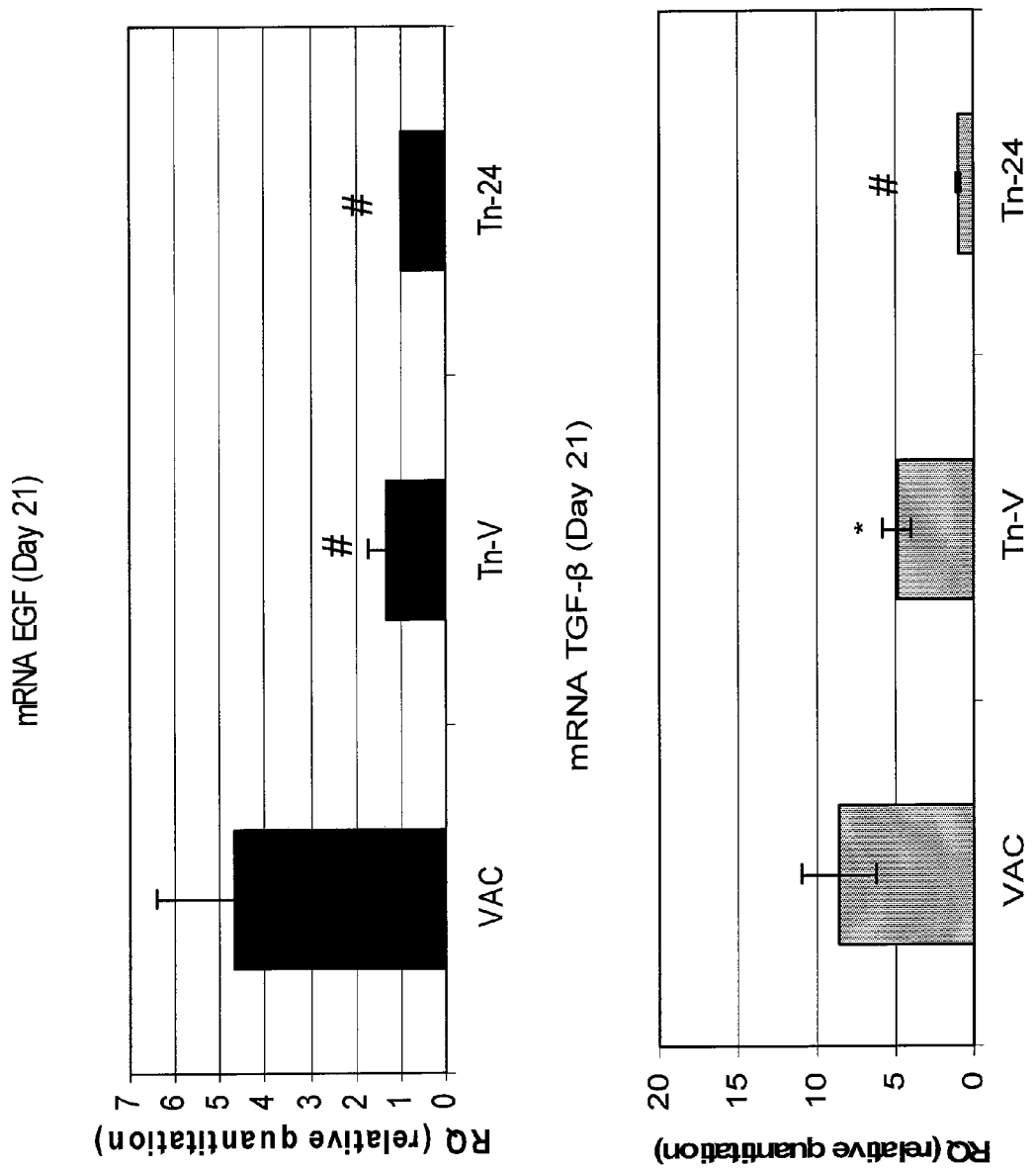
FIG. 9. shows the mRNA Expression of wound healing related growth factors of the groups in Example 4.

FIG. 9. shows the mRNA Expression of wound healing related growth factors of the experimental and control conditions. mRNA expression levels of TGF-β and EGF of tissues harvested at day 21. EGF mRNA is suppressed in group Tn-24 and Tn-V, both treated with thin sNAG membranes. TGF-B also has suppressed mRNA levels, especially in group Tn-24 that had a 24 wound activation with sNAG prior application of the VAC dressing. *<0.05 vs. VAC Group, #<0.01 vs VAC Group.

We conclude that the combination of early prior treatment with sNAG nanofibers, and polyurethane VAC foam interfaces can achieve improved wound healing and superior granulation tissue formation in diabetic non-healing wounds.

The invention claimed is:

1. A system that delivers sub-atmospheric pressure to a wound for the purpose of wound healing and hemostasis that includes:
    a) a device that delivers a vacuum pressure in the range of 0 to 250 mm Hg;
    b) a seal that is semipermeable that covers the wound;
    c) a tube connecting the device to the seal; and
    d) a hemostatic appliance for application to the wound below the seal comprising
        (i) a support that promotes uniform distribution of pressure within the wound and
        (ii) a hemostatic agent attached to the support wherein the hemostatic agent is composed of poly-N-acetylglucosamine with a mean fiber size of less than about 10 microns.

2. The system of claim 1, wherein the support comprises a porous sponge.

3. The system of claim 2, wherein the sponge has a pore size of greater than 10microns and less than 500 microns.

4. The system of claim 1, wherein the hemostatic agent is composed of collagen with a mean fiber length of 0.01 to 5 microns in size.

5. The system of claim 1, wherein the hemostatic agent composed of collagen, of Type I.

6. The system of claim 1, wherein the hemostatic agent is composed of collagen that has been dispersed in a solution greater than pH 3.2.

7. The system of claim 1, wherein the hemostatic agent is composed of collagen that has a biodegradation time of 0.5 to 10 days.

8. The system of claim 1, wherein the hemostatic agent is composed of collagen that has a thickness on the support of 0.01 to 100 microns.

9. The system of claim 1 wherein the hemostatic agent further comprises a material selected from the group consisting of fibrin, thrombin, oxidized regenerated cellulose, chitin, chitosan, calcium alginate, cryoprecipate, platelets and blood clotting cascade factors including Factor VII, VIII, IX.

10. A wound healing appliance for use with a negative pressure comprising:
    a) a support that promotes a uniform distribution of pressure within a wound; and
    b) a hemostatic agent attached to the support wherein the hemostatic agent is composed of poly-N-acetylglucosamine with a mean fiber size of less than about 10 microns.

11. The appliance of claim 10, wherein the support comprises a porous sponge.

12. The appliance of claim 11, wherein the sponge has a pore size of greater than 10microns and less than 500 microns.

13. The appliance of claim 10, wherein the hemostatic agent is composed of collagen with a mean fiber length of 0.01 to 5 microns in size.

14. The appliance claim 13, wherein the collagen is composed of fibers and the fibers have a mean fiber length of 0.01 to 5 microns.

15. The appliance of claim 13, wherein the collagen, is of Type I.

16. The appliance of claim 10, wherein the hemostatic agent comprises collagen that has been dispersed in a solution greater than pH 3.2.

17. The appliance of claim 10, wherein the hemostatic comprises a material that has a biodegradation time of 0.5 to 10 days.

18. The appliance of claim 10 wherein the support comprises a screen.

19. The appliance of claim 18 wherein the hemostatic agent comprises collagen.

20. The appliance of claim 19 wherein the collagen is disposed on the screen at a thickness of 0.01 to 100 microns.

21. The appliance of claim 10 wherein the hemostatic agent comprises a material selected from the group consisting of fibrin, thrombin, oxidized regenerated cellulose, chitin, chitosan, calcium alginate, cryoprecipate, platelets and blood clotting cascade factors including Factor VII, VIII, IX.

22. The appliance of claim 10 wherein the support is a foam.

23. A system that delivers sub-atmospheric pressure to a wound for the purpose of wound healing and hemostasis that includes:
   a) a device that delivers a vacuum pressure in the range of 0 to 250 mm Hg;
   b) a seal that is semipermeable that covers the wound;
   c) a tube connecting the device to the seal; and
   d) an appliance for application to the wound below the seal wherein the appliance:
      (i) is hemostatic,
      (ii) improves wound healing, and
      (iii) has a bioreactivity rating of less than 1.5, wherein the bioactivity rating is calculated by grading one or more categories from among an inflammatory response or a healing response.

24. A method of promoting wound healing comprising:
   (a) providing a hemostatic appliance comprising a support that promotes uniform distribution of pressure within a wound and a hemostatic agent comprising a poly-N-acetylglucosamine with a mean fiber size of less than about 10 microns attached to the support;
   (b) applying the hemostatic appliance to the wound so as to at least partially cover the wound; and
   (c) applying a vacuum pressure in the range of 0 to 250 mm Hg to the hemostatic appliance and the wound.

25. The method of claim 24 wherein step (b) occurs at least 12 hours before step (c).

26. The method of claim 25 wherein step (b) occurs at least 18 hours before step (c).

27. The method of claim 26 wherein step (b) occurs about 24 hours before step (c).

* * * * *